US012329989B2

(12) United States Patent
Miyoshi et al.

(10) Patent No.: US 12,329,989 B2
(45) Date of Patent: Jun. 17, 2025

(54) PARTICLE THERAPY SYSTEM, IRRADIATION CONTROL APPARATUS, AND IRRADIATION CONTROL METHOD

(71) Applicant: Hitachi High-Tech Corporation, Tokyo (JP)

(72) Inventors: Takuto Miyoshi, Tokyo (JP); Takuya Nomura, Tokyo (JP); Yuki Ito, Tokyo (JP); Takashi Toyoda, Tokyo (JP); Takahiro Yamada, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 470 days.

(21) Appl. No.: 17/945,180

(22) Filed: Sep. 15, 2022

(65) Prior Publication Data

US 2024/0091560 A1     Mar. 21, 2024

(30) Foreign Application Priority Data

Nov. 11, 2021   (JP) .................................. 2021-184227

(51) Int. Cl.
*A61N 5/10*     (2006.01)

(52) U.S. Cl.
CPC .................................. *A61N 5/1071* (2013.01)

(58) Field of Classification Search
CPC .................................................. A61N 5/1071
See application file for complete search history.

(56) References Cited

U.S. PATENT DOCUMENTS

| | | | |
|---|---|---|---|
| 11,198,022 B1 | 12/2021 | Tansho et al. | |
| 2007/0194222 A1 | 8/2007 | Takayama et al. | |
| 2010/0171047 A1 | 7/2010 | Matsuda et al. | |
| 2012/0181442 A1 | 7/2012 | Prieels | |
| 2012/0305796 A1 | 12/2012 | Iseki et al. | |
| 2013/0190548 A1 | 7/2013 | Honda et al. | |
| 2013/0231517 A1 | 9/2013 | Iwamoto et al. | |
| 2014/0061498 A1* | 3/2014 | Honda ................. | A61N 5/1075 250/397 |
| 2015/0087885 A1 | 3/2015 | Boisseau et al. | |
| 2015/0099917 A1 | 4/2015 | Bula et al. | |
| 2015/0273241 A1 | 10/2015 | Ito et al. | |
| 2020/0298020 A1 | 9/2020 | Goebel et al. | |

FOREIGN PATENT DOCUMENTS

| | | |
|---|---|---|
| CN | 112379401 A | 2/2021 |
| EP | 1 621 228 A1 | 2/2006 |
| JP | 2002-228755 A | 8/2002 |
| JP | 2007-212242 A | 8/2007 |
| JP | 2013-500465 A | 1/2013 |
| JP | 6807125 B | 1/2021 |
| JP | 2021-194349 A | 12/2021 |

OTHER PUBLICATIONS

Extended European Search Report received in corresponding European Application No. 22195509.9 dated Mar. 30, 2023.

* cited by examiner

*Primary Examiner* — Nicole M Ippolito

(74) *Attorney, Agent, or Firm* — MATTINGLY & MALUR, PC

(57) ABSTRACT

A dose monitor measures a dose of a beam. The position monitor measures the beam size of the beam. The irradiation control apparatus calculates the measurement characteristic of the dose monitor based on the dose and the beam size of the beam, and controls the irradiation of the patient with the beam based on the measurement characteristic and the dose.

11 Claims, 11 Drawing Sheets

POSITION OF SMALL ELECTRODE IN X DIRECTION

PARTICLE THERAPY SYSTEM, IRRADIATION CONTROL APPARATUS, AND IRRADIATION CONTROL METHOD

CROSS-REFERENCE TO RELATED APPLICATION

The present application claims priority from Japanese application JP2021-184227, filed on Nov. 11, 2021, the contents of which is hereby incorporated by reference into this application.

BACKGROUND OF THE INVENTION

1. Field of the Invention

The present disclosure relates to a particle therapy system, an irradiation control apparatus, and an irradiation control method.

2. Description of the Related Art

In recent years, a particle therapy for irradiating a tumor of a patient with particle beams such as a proton beam and a carbon beam has attracted attention. The particle therapy uses a phenomenon called a Bragg peak in which a high dose is applied to the surroundings immediately before a particle beam stops, and it is thus possible to form a dose distribution matching the shape of a tumor more easily as compared with an X-ray therapy or the like. As a result, implementation of a highly accurate radiotherapy is expected.

In the particle therapy, a charged particle beam (hereinafter, simply referred to as a particle beam) accelerated by an accelerator system including a linear accelerator, a synchrotron, or the like is transported as a particle beam to an irradiation nozzle, and is used to irradiate a tumor in a patient's body. Examples of a main beam irradiation method include a passive method and a scanning method. The passive method is a method of matching the shape of a particle beam to the shape of a tumor by expanding a spot size using a scatterer, a ridge filter, a collimator, a patient bolus, or the like. The scanning method is a method in which an irradiation direction of a thin particle beam called a pencil beam is adjusted by a scanning magnet in a container called an irradiation nozzle, and each of a plurality of minute regions (hereinafter, referred to as spots) virtually set in a tumor is sequentially irradiated with the particle beam to irradiate the entire tumor. In addition, examples of the scanning method include a spot scanning irradiation method in which movement between spots is performed in a state where a particle beam is stopped, and a raster scanning irradiation method in which movement between spots is performed in a state where irradiation with a particle beam is performed. In recent years, since it is possible to cope with a complicated tumor shape and its change, facilities adopting the scanning method are increasing.

In the scanning method, a particle beam is monitored by a position monitor and a dose monitor installed in the irradiation nozzle, and an irradiation dose is controlled for each spot based on the monitoring result. The position monitor measures the center position and size of a particle beam, and the dose monitor measures the magnitude of a dose. The irradiation control apparatus calculates an integral dose which is an integral value of irradiation doses with which the spot is irradiated based on these measured values, and once the integral dose reaches a target dose (hereinafter, referred to as a prescription) set in advance for each spot, the irradiation control apparatus performs irradiation of the next spot with a beam. Therefore, in order to suppress damage to surrounding healthy tissues while applying a sufficient dose to a tumor, high measurement accuracy is required for the position monitor and the dose monitor.

However, there is a known problem that, in the dose monitor, a dose rate, which is a dose detected per unit time, affects measurement accuracy. An ionization chamber, which is a general dose monitor, is a container in which gaps between a plurality of electrodes are filled with a fluid such as a gas or a liquid, and when a particle beam is incident, the fluid is ionized on a trajectory of the particle beam, whereby cations and electrons are generated. As a voltage is fed between electrodes, each of cations and electrons move to the opposite electrode, so that a current flows between the electrodes only for a short time. The dose is calculated by measuring the current. However, since the density of the generated cations increases as the dose rate increases, a ratio at which the cations and the electrons recombine before reaching the electrode increases, and collection efficiency in collecting the cations and the electrons in the dose monitor decreases.

In the particle therapy according to the related art, since the dose rate is relatively low, the decrease in collection efficiency of the dose monitor is about 1%, and an influence on a linear responsiveness of the dose monitor is small. However, in recent years, a radiotherapy with an ultra-high dose rate called FLASH radiotherapy has attracted attention, and there is an increasing demand for irradiation with a higher dose rate than that according to the related art. A high dose rate may cause a decrease in collection efficiency of the ionization chamber by about several 10%, and in this case, the linear responsiveness of the dose monitor is poor. Therefore, in order to control a dose applied to a subject with high accuracy, it is required to grasp the collection efficiency of the dose monitor.

JP 6807125 B2 discloses a technology for correcting collection efficiency of an ionization chamber based on a prescription prepared in advance. In this technology, the dose rate and size of a beam with which a patient is irradiated at the time of treatment are estimated as beam parameters based on a prescription. A correction coefficient for correcting a preset collection efficiency is determined for each spot based on the beam parameters.

SUMMARY OF THE INVENTION

However, since the beam parameter varies during irradiation with a particle beam, a beam parameter estimated based on a prescription and a beam parameter of an actually emitted particle beam do not always match. In particular, in irradiation with a particle beam at a high dose rate, the variation of the beam parameter is not negligible. Therefore, in the technology described in JP 6807125 B2, the collection efficiency of the dose monitor cannot be appropriately corrected, and it is difficult to accurately control a dose of a particle beam with which a subject is irradiated.

The present disclosure has been made in view of the above circumstances, and an object of the present disclosure is to provide a particle therapy system, an irradiation control apparatus, and an irradiation control method capable of more accurately controlling a dose of a particle beam with which a subject is irradiated.

A particle therapy system according to an aspect of the present disclosure is a particle therapy system that irradiates a subject with a particle beam, the particle therapy system including: a dose monitor that measures a dose of the particle beam; a position monitor that measures a beam size of the particle beam; and an irradiation control apparatus that calculates a measurement characteristic obtained by correcting a measurement characteristic of the dose monitor based on the dose and the beam size, and controls irradiation of the subject with the particle beam based on the measurement characteristic and the dose.

According to the present invention, it is possible to control a dose of a particle beam more accurately with which a subject is irradiated.

DESCRIPTION OF THE PREFERRED EMBODIMENTS

Hereinafter, embodiments of the present disclosure will be described with reference to the drawings.

First Embodiment

First, a particle therapy system and an irradiation control apparatus according to a first embodiment of the present disclosure will be described with reference to FIGS. 1 to 9.

Figure 1:
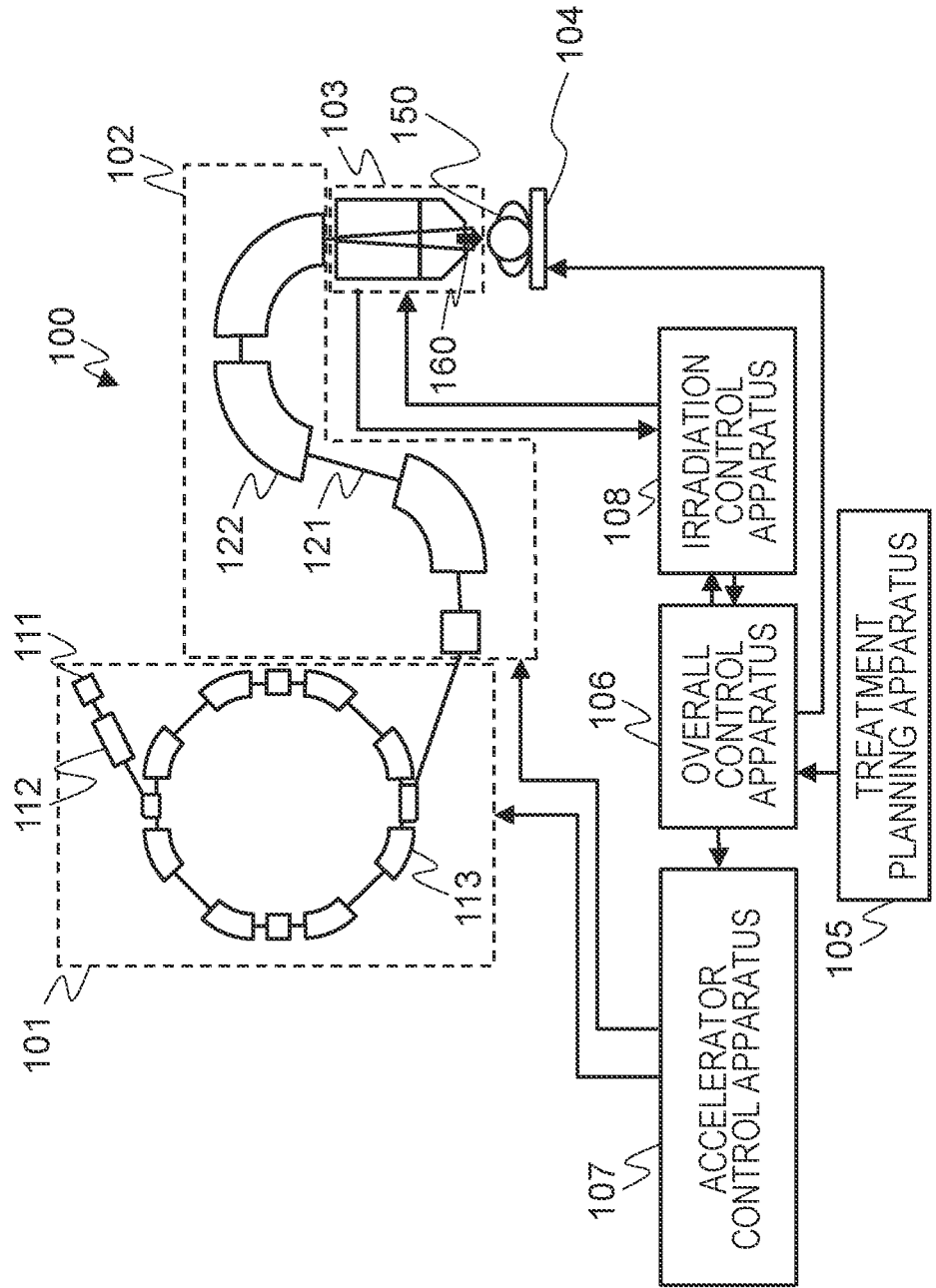
FIG. 1 is a diagram illustrating an overall configuration of a particle therapy system according to a first embodiment of the present disclosure.

FIG. 1 is a diagram illustrating an overall configuration of the particle therapy system according to the present embodiment. A particle therapy system 100 illustrated in FIG. 1 is a system that irradiates a patient 150 who is a subject with a beam 160 which is a particle beam. In the present embodiment, the particle therapy system 100 uses a spot scanning irradiation method or a raster scanning irradiation method in which spots which are a plurality of minute regions virtually set in the body of the patient 150 are sequentially irradiated.

As illustrated in FIG. 1, the particle therapy system 100 includes an accelerator system 101, a beam transport system 102, an irradiation nozzle 103, a couch 104, a treatment planning apparatus 105, an overall control apparatus 106, an accelerator control apparatus 107, and an irradiation control apparatus 108.

The accelerator system 101 is an apparatus group that generates and extracts the beam 160. In the example in FIG. 1, the accelerator system 101 includes an ion source 111, an injector 112, and a synchrotron accelerator 113. The ion source 111 generates charged particles that are particles constituting the beam 160. The injector 112 injects the charged particles generated by the ion source 111 into the synchrotron accelerator 113. The synchrotron accelerator 113 accelerates the charged particles injected from the injector 112 to generate and output the beam 160.

Note that the accelerator system 101 illustrated in FIG. 1 is merely an example, and is not limited to this example. For example, the accelerator system 101 may be an apparatus group using a cyclotron accelerator or a synchrocyclotron accelerator instead of the synchrotron accelerator 113.

The beam transport system 102 is an apparatus group that transports the beam 160 extracted from the accelerator system 101 to the irradiation nozzle 103. The beam transport system 102 includes a beam path 121 and a bending magnet 122. The beam path 121 is a path through which the beam 160 passes, and connects the accelerator system 101 and the irradiation nozzle 103. The beam path 121 is in a vacuum state. The bending magnet 122 bends the beam passing through the beam path 121 by a magnetic field and transports the beam to the irradiation nozzle 103. The beam transport system 102 may include or does not have to include a rotating gantry that adjusts an irradiation angle at which the patient 150 is irradiated with the beam 160.

The irradiation nozzle 103 is an apparatus container including an apparatus group that includes an apparatus for irradiating the patient 150 with the beam 160 transported from the beam transport system 102 and an apparatus for measuring a beam parameter which is a parameter related to the beam 160. A more detailed configuration of the irradiation nozzle 103 will be described below with reference to FIG. 2.

The couch 104 is a bed on which the patient 150 is placed. The couch 104 changes the position and posture (angle) of the patient 150 to a desired position and posture by moving based on an instruction from the overall control apparatus 106. The couch 104 can perform movement in six axial directions including, for example, translational movement along each of three different axes and rotational movement around each of the three axes.

The treatment planning apparatus 105 performs treatment planning for the patient 150, creates a prescription, and transmits the prescription to the overall control apparatus 106. The prescription indicates, for each spot irradiated with the beam 160, a target dose which is a target value of a dose of the beam 160 with which each spot is irradiated.

The overall control apparatus 106 is connected to the couch 104, the treatment planning apparatus 105, the accelerator control apparatus 107, and the irradiation control apparatus 108, and controls each connected device based on the prescription from the treatment planning apparatus 105.

The accelerator control apparatus 107 controls the accelerator system 101 and the beam transport system 102 based on an instruction from the overall control apparatus 106.

The irradiation control apparatus 108 controls the irradiation nozzle 103 based on an instruction from the overall control apparatus 106. Further, the irradiation control apparatus 108 processes a result of measurement using the irradiation nozzle 103 and transfers the processed result to the overall control apparatus 106. A more detailed configuration of the irradiation control apparatus 108 will be described below with reference to FIG. 6.

The treatment planning apparatus 105, the overall control apparatus 106, the accelerator control apparatus 107, and the irradiation control apparatus 108 are implemented by, for example, a computer system including a central processing unit (CPU), a memory, a storage apparatus, a communication interface apparatus, a user interface (UI) apparatus, and the like. Each of these apparatuses performs various processings, for example, by the central processing unit reading and executing a program recorded in the memory. The program of each apparatus may be a single program, may be divided into a plurality of programs, or may be a combination thereof. Some or all of the programs may be implemented by dedicated hardware or may be modularized. In addition, some or all of the programs may be installed in each apparatus by using a program distribution server (not illustrated), an external storage medium, or the like. The apparatuses may each be implemented as an independent apparatus and may be connected to each other by a wired or wireless network, or two or more apparatuses may be integrated.

Figure 2:
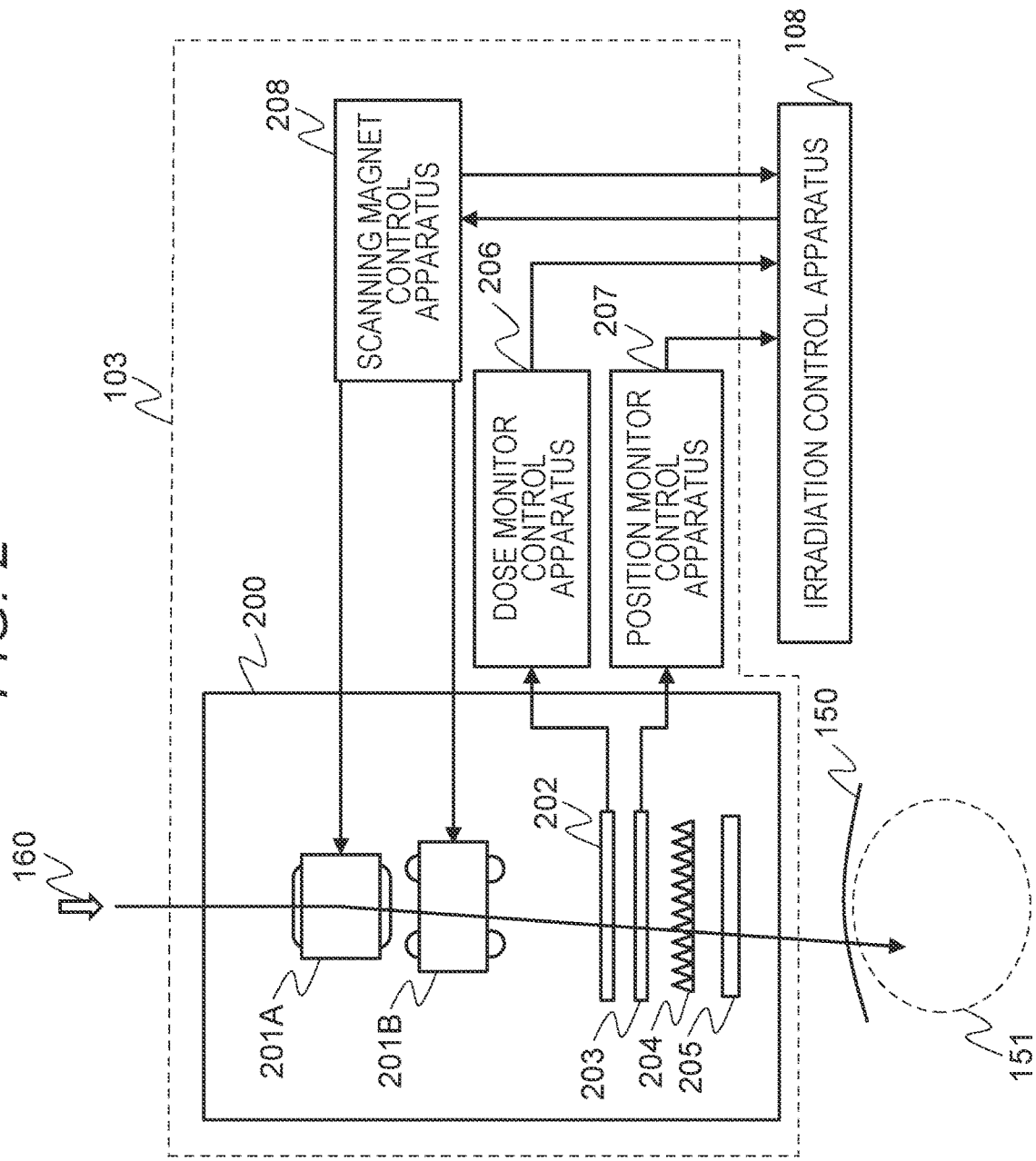
FIG. 2 is a diagram illustrating a configuration of an irradiation nozzle according to the first embodiment of the present disclosure.

FIG. 2 is a diagram illustrating a configuration example of the irradiation nozzle 103.

The irradiation nozzle 103 illustrated in FIG. 2 includes an irradiation system 200 for irradiating the patient 150 with the beam 160, and a dose monitor control apparatus 206, a position monitor control apparatus 207, and a scanning magnet control apparatus 208 which are control systems that control the irradiation system 200. The irradiation system 200 includes scanning magnets 201A and 201B, a dose monitor 202, and a position monitor 203.

Note that the irradiation system 200 may include a ridge filter 204 that enlarges a Bragg peak of the beam 160 in a traveling direction of the beam 160 and a range shifter 205 that adjusts a depth to be reached by the beam 160, as necessary.

The scanning magnets 201A and 201B are scanning systems that scan the beam 160 in a plane (two-dimensional direction) orthogonal to a passing direction of the beam 160. A target volume 151 in the patient 150 is irradiated with the beam 160 scanned by the scanning magnets 201A and 201B. The target volume 151 is an irradiation region irradiated with the beam 160. For example, in a case where the particle therapy system 100 treats a tumor such as a cancer of the patient 150, the target volume 151 is a region obtained by adding a margin (a margin region considering an error in an irradiation position) to a tumor region where the tumor is present. The spot irradiated with the beam 160 is set in the target volume 151.

The dose monitor 202 is a monitor for measuring a dose rate of the beam 160 with which each spot is irradiated. The dose monitor 202 outputs a detection signal indicating a measurement result to the dose monitor control apparatus 206. The dose monitor control apparatus 206 calculates the dose rate of the beam 160 with which each spot is irradiated based on the detection signal from the dose monitor 202, and outputs the dose rate to the irradiation control apparatus 108.

Figure 3:
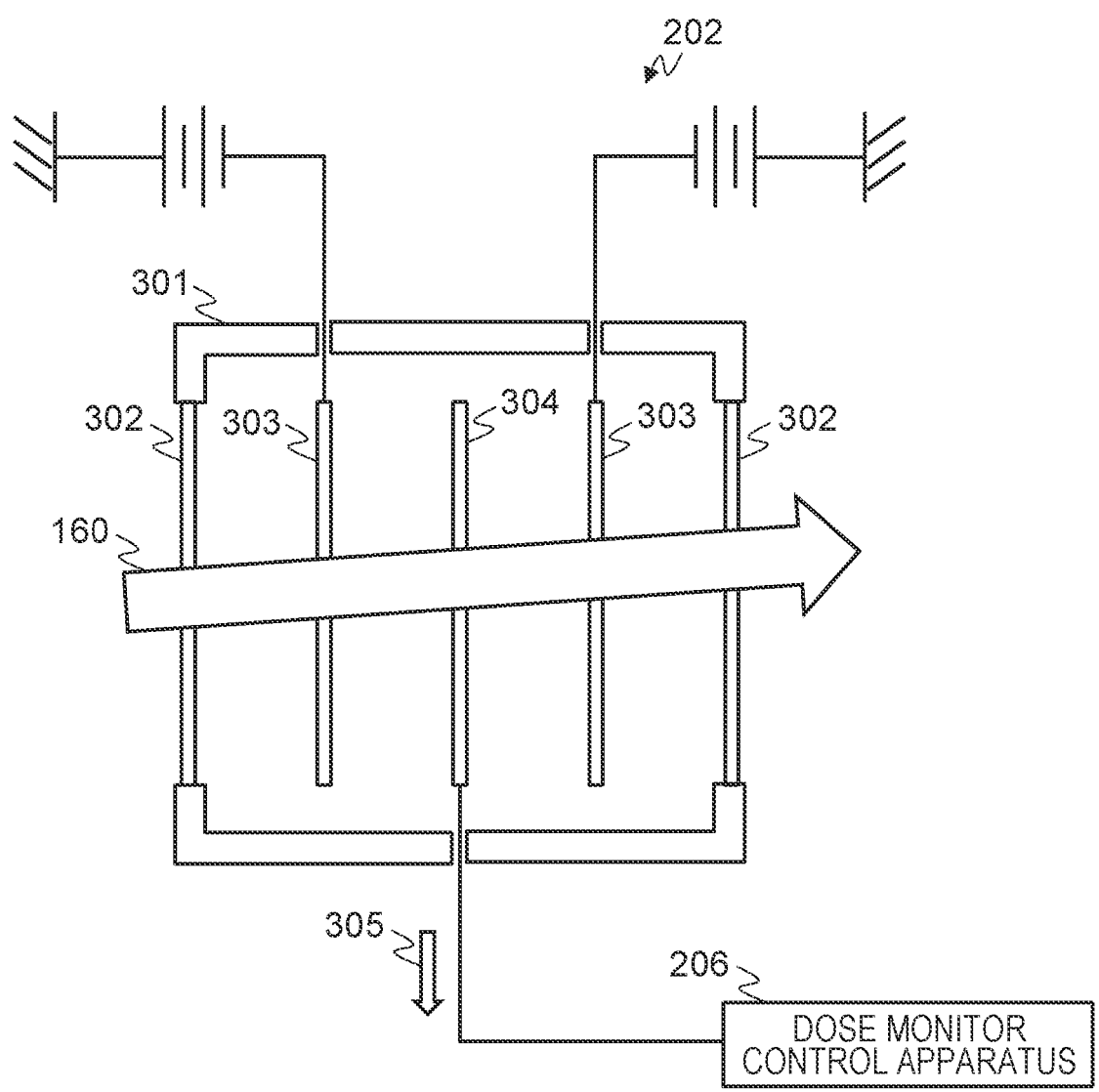
FIG. 3 is a diagram illustrating an example of a configuration of a dose monitor according to the first embodiment of the present disclosure.

FIG. 3 is a diagram illustrating an example of the dose monitor 202. The dose monitor 202 illustrated in FIG. 3 is a commonly used parallel plate ionization chamber.

The dose monitor 202 which is a parallel plate ionization chamber illustrated in FIG. 3 is covered with a shielding wall 301, and a plurality of beam windows 302 having a high transmittance with respect to the beam 160 are formed in the shielding wall 301. Specifically, the beam windows 302 are formed at positions facing each other in the shielding wall 301, so that a beam 160 entering from one beam window 302 is extracted from the other beam window. In a space surrounded by the shielding wall 301, one or more flat plate-shaped high-voltage electrodes 303 and one or more flat plate-shaped collector electrodes 304 are arranged in parallel. In the example in FIG. 3, the dose monitor 202 includes one collector electrode 304 and two high-voltage electrodes 303 provided while having the collector electrode 304 interposed therebetween. A high voltage is fed to the high-voltage electrode 303, and an electric field is generated between the high-voltage electrode 303 and the collector electrode 304. In addition, a space between the respective electrodes 303 and 304 is filled with gas.

The beam 160 that has passed through the beam window 302 and has entered the dose monitor 202 ionizes the gas between the electrodes 303 and 304 to generate cations and electrons. The generated cations and electrons move to the collector electrode 304 by an electric field generated between the electrodes 303 and 304. A current 305 flows between the electrodes 303 and 304 by the movement of the cations and electrons, and is measured by the dose monitor control apparatus 206.

A proportional relationship is established between the dose of the beam 160 and the number of ions generated. Therefore, the dose monitor control apparatus 206 calculates the dose rate of the beam 160 based on the current 305 by multiplying the value of the current 305 by an appropriate coefficient. The dose rate calculated by the dose monitor control apparatus 206 is a dose rate before correction that is a dose rate that does not take into consideration a variation in collection efficiency of the dose monitor 202.

The dose monitor 202 is not limited to the example illustrated in FIG. 3. For example, the space between the electrodes 303 and 304 may be filled with liquid or opened to air. The shape of each of the electrodes 303 and 304 is not limited to the flat plate shape, and may be, for example, a coaxial cylindrical shape. The dose monitor 202 is not limited to the ionization chamber, and may be any monitor as long as a measurement characteristic changes according to the dose rate and the beam size.

The description returns to FIG. 2. The position monitor 203 is a monitor for measuring the center position and the beam size of the beam 160. The position monitor 203 outputs a detection signal indicating a measurement result to the position monitor control apparatus 207. The position monitor control apparatus 207 calculates the center position and the beam size of each beam based on the detection signal input from the position monitor 203, and outputs the center position and the beam size to the irradiation control apparatus 108.

Figure 4:
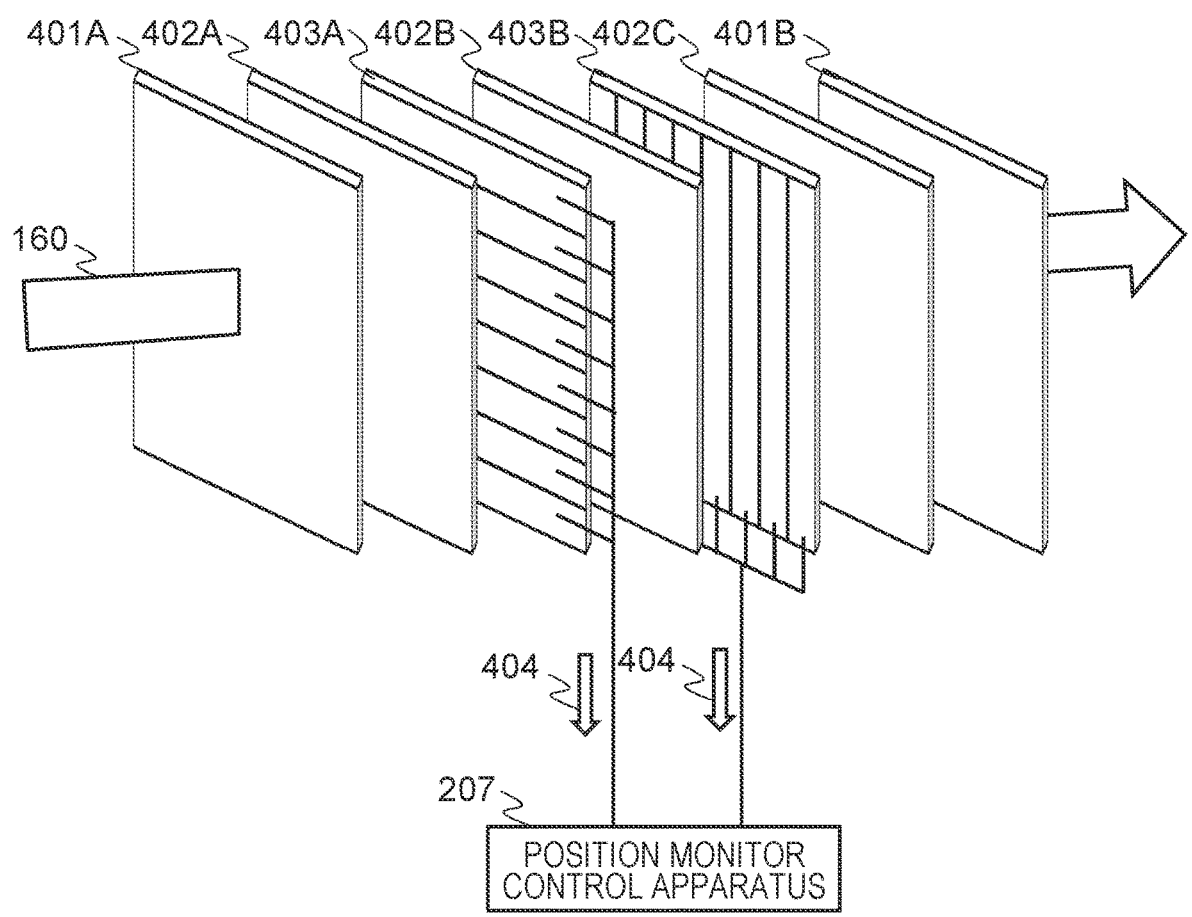
FIG. 4 is a diagram illustrating an example of a configuration of a position monitor according to the first embodiment of the present disclosure.

FIG. 4 is a diagram illustrating an example of the position monitor 203. The position monitor 203 illustrated in FIG. 4 is a commonly used multi-strip ionization chamber.

Similarly to the dose monitor 202 illustrated in FIG. 3, the multi-strip ionization chamber serving as the position monitor 203 is covered with a shielding wall (not illustrated), and a plurality of beam windows 401 having a high transmittance with respect to the beam 160 are formed in the shielding wall. Specifically, the beam windows 401 are formed at positions facing each other in the shielding wall, so that a beam 160 entering from one beam window 401 is extracted from the other beam window. In a space surrounded by the shielding wall, one or more flat plate-shaped high-voltage electrodes 402 and one or more flat plate-shaped collector electrodes 403A and 403B are arranged in parallel. A high voltage is fed to the high-voltage electrode 402, and an electric field is generated between the high-voltage electrode 402 and the collector electrodes 403A and 403B. A space between the electrodes 402, 403A, and 403B is filled with a fluid such as a gas or a liquid.

The collector electrode 403A is implemented by a plurality of strip-shaped small collector electrodes arranged in parallel in one direction (X direction) in the plane, and the collector electrode 403B is implemented a plurality of strip-shaped small collector electrodes arranged in parallel in a direction (Y direction) orthogonal to the X direction in the plane.

The beam 160 that has passed through the beam window 401 and has entered the position monitor 203 ionizes the fluid between the electrodes 402 and 403 to generate cations and electrons. The generated cations and electrons move to each small collector electrode of the collector electrode 403A or 403B in the vicinity by the electric field generated between the electrodes 402 and 403, and a current 404 is generated by the movement of the cations and electrons and is measured for each small collector electrode by the position monitor control apparatus 207. As a result, the position monitor control apparatus 207 can measure not only a two-dimensional ion generation distribution, but also a dose distribution in the in-plane direction of the collector electrode 403A or 403B based on the current 404 for each small collector electrode, and can calculate the center position and the beam size of the beam 160 based on the dose distribution.

Figure 5:
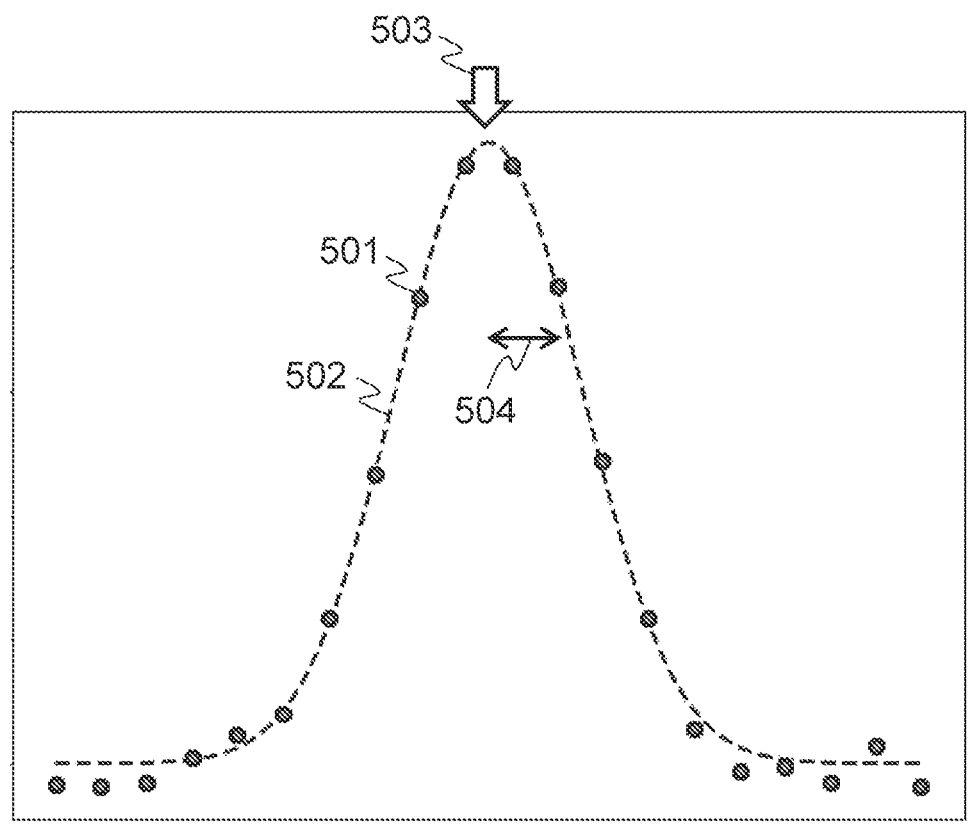
FIG. 5 is a diagram for describing an example of a method of calculating a center position and a size of a beam according to the first embodiment of the present disclosure.

FIG. 5 is a diagram for describing an example of a calculation method of calculating the center position and the beam size of the beam 160. In FIG. 5, the horizontal axis represents the center position of each small collector electrode of the collector electrode 403A in the X direction, and the vertical axis represents a current value. Each data point 501 in FIG. 5 represents a current value indicated by a detection signal of each small collector electrode.

Assuming that the shape of the beam 160 follows the Gaussian distribution, a peak position 503 and a standard deviation 504 when a distribution of the data point 501 is approximated by a Gaussian function 502 are the center position and the beam size of the beam 160, respectively. Although FIG. 5 illustrates an example of a one-dimensional distribution for simplicity, actually, a two-dimensional dose distribution is approximated by a two-dimensional Gaussian function.

The method of calculating the center position and the beam size of the beam 160 is not limited to the above example, and the dose distribution may be approximated by a Lorentz function on the assumption that the shape of the beam 160 follows the Lorentz distribution. Furthermore, the position monitor 203 is not limited to the example illustrated in FIG. 3. For example, the position monitor 203 may be a multi-wire ionization chamber or the like.

The description returns to FIG. 2. The irradiation control apparatus 108 calculates the irradiation position of the beam 160 based on the center position of the beam 160 calculated by the position monitor control apparatus 207. In addition, the irradiation control apparatus 108 calculates collection efficiency that is the measurement characteristic of the dose monitor 202 based on the beam parameters (the dose rate, the center position, and the beam size) transmitted from the dose monitor control apparatus 206 and the position monitor control apparatus 207. The irradiation control apparatus 108 corrects the dose rate calculated by the dose monitor control apparatus 206 based on the collection efficiency to calculate a corrected dose rate in consideration of a variation in collection efficiency.

Next, an operation of the particle therapy system 100 will be described.

Figure 6:
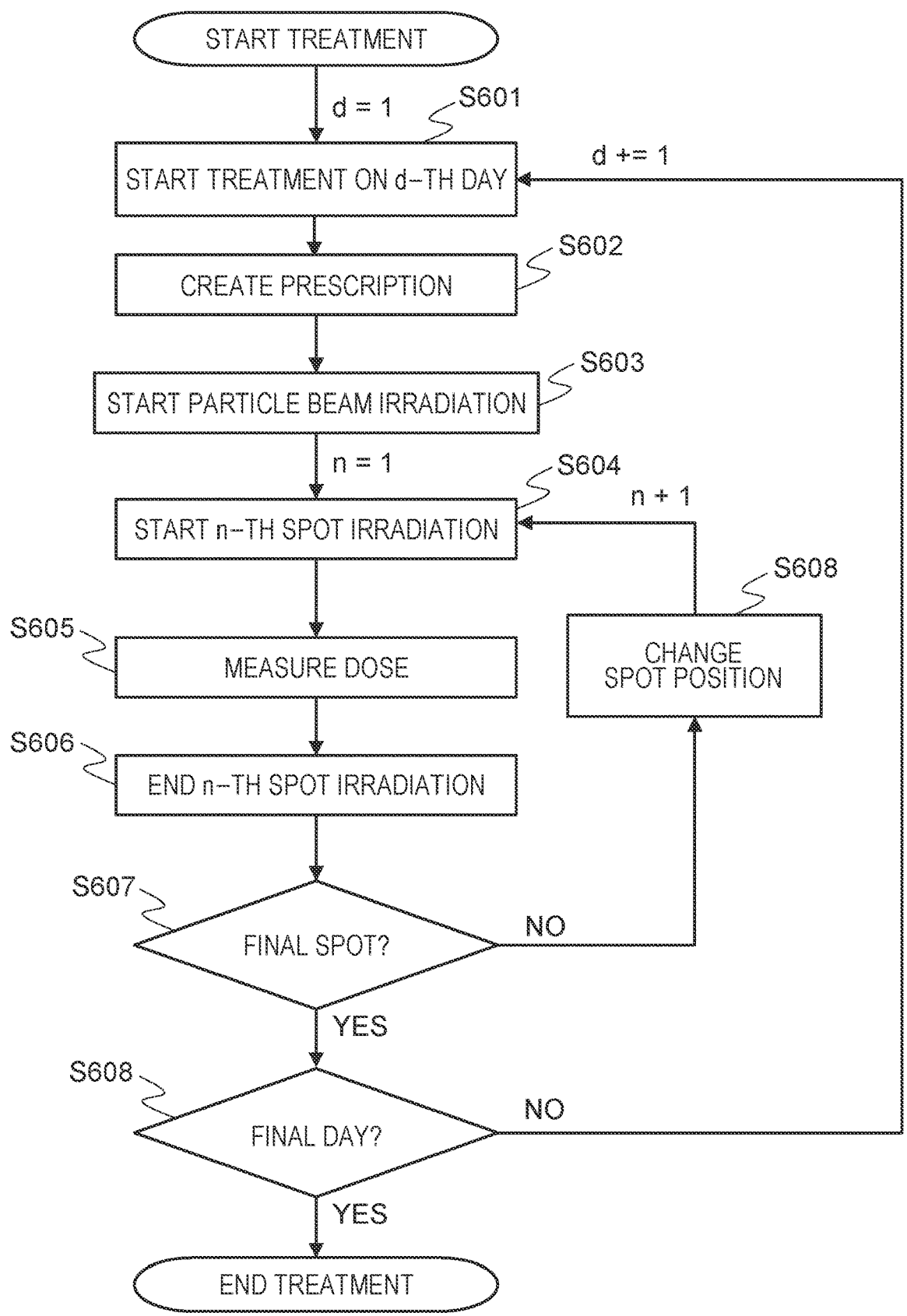
FIG. 6 is a flowchart for describing an operation for a particle therapy according to the first embodiment of the present disclosure.

FIG. 6 is a flowchart for describing an example of treatment processing of treating the patient 150 by the particle therapy system 100.

In the particle therapy, usually, the high-dose beam 160 is applied to the patient 150 at a time, and thus, in order to suppress a normal tissue of the patient 150 from being damaged, divided irradiation in which the patient 150 is dividedly irradiated with the beam a plurality of times is performed. In the present embodiment, a unit of division is one day, and the number of times the irradiation with the beam is dividedly performed is 30. However, the unit of division and the number of times the irradiation with the beam is dividedly performed are not limited to these examples. For example, the unit of division does not need to be one day, and the treatment may be performed a plurality of times per day.

First, once a treatment on the day (d-th day) starts (Step S601), the treatment planning apparatus 105 creates a prescription as a treatment plan (Step S602). An initial value of d is 1.

Specifically, in Step S602, the treatment planning apparatus 105 first reads an in-vivo image showing the periphery of a tumor that is a target volume of the patient 150, and converts a thickness distribution from the body surface of the patient 150 to the target volume into a water equivalent thickness ratio distribution based on the in-vivo image. The in-vivo image is created by, for example, a computed tomography (CT) examination or the like. The water equivalent thickness ratio is a ratio of the thickness of water to the thickness of a local medium that causes the same energy loss for the beam 160 and is a physical quantity that determines a stopping distance of the beam 160.

Subsequently, the treatment planning apparatus 105 uses the in-vivo image to determine a contour of the target volume 151, which is a three-dimensional irradiation region irradiated with the beam 160. For example, the treatment planning apparatus 105 displays the in-vivo image, causes an operator such as a doctor to draw a contour of a tumor, and determines the contour of the target volume 151 by giving a predetermined margin to the contour of the tumor.

Furthermore, the treatment planning apparatus 105 creates a prescription (a target dose set for each spot). Specifically, the treatment planning apparatus 105 first sets a target dose for the target volume 151. The target dose is input by an operator, for example. The treatment planning apparatus 105 creates a prescription by calculating the position of a spot for applying the target dose to the target volume 151 and the target dose by using a predetermined optimization calculation method or the like based on the water equivalent thickness ratio distribution. The treatment planning apparatus 105 displays the prescription, and once the operator approves the prescription, the treatment planning apparatus 105 transmits the prescription to the overall control apparatus 106.

The overall control apparatus 106 creates control instruction data for controlling the accelerator control apparatus 107 and the irradiation control apparatus 108 for each spot based on the prescription from the treatment planning apparatus 105, and transmits the control instruction data to the accelerator control apparatus 107 and the irradiation control apparatus 108. The transmitted data is stored in a memory (not illustrated) in the accelerator control apparatus 107 and the irradiation control apparatus 108. Examples of the control instruction data for the accelerator control apparatus 107 include an excitation current value of each magnet of the accelerator system 101 and the beam transport system 102 determined according to beam energy corresponding to the depth of a spot position, a radio frequency power value fed to a radio frequency accelerating cavity, and the like. In addition, the control instruction data for the irradiation control apparatus 108 includes a target dose, current values of the scanning magnets 201A and 201B, and the like.

Then, the processing of Step S602 ends. In a case where the prescription is not approved by the operator, the target dose is reset.

Thereafter, the patient 150 is placed on the couch 104, the position of the patient 150 is adjusted in such a way as to match with that at the time of capturing the in-vivo image, and the operator instructs the particle therapy system 100 to perform irradiation with the beam 160 (Step S603).

Then, the overall control apparatus 106 transmits an irradiation start instruction for a spot to be irradiated (referred to as the n-th spot) to the accelerator control apparatus 107 and the irradiation control apparatus 108 (Step S604). An initial value of n is 1.

Once the irradiation start instruction is received, the accelerator control apparatus 107 starts acceleration of the beam 160 according to the control instruction data stored in the memory. Once the acceleration of the beam 160 is completed, the irradiation control apparatus 108 changes the current values of the scanning magnets 201A and 201B via the scanning magnet control apparatus 208. Once the change of the current values is completed, the accelerator control apparatus 107 extracts the beam 160. The extracted beam 160 passes through the beam transport system 102 and the irradiation nozzle 103 to irradiate the target volume 151 of the patient 150. The dose monitor 202 and the position monitor 203 measure the beam parameters of the beam 160, and the irradiation control apparatus 108 calculates the dose of the beam 160 for the n-th spot based on the beam parameters (Step S605).

Thereafter, once the dose reaches the target dose, the irradiation control apparatus 108 transmits an end signal indicating the end of irradiation of the n-th spot with the beam 160 to the overall control apparatus 106. Once the end signal is received, the overall control apparatus 106 performs end processing which is processing of ending the irradiation of the n-th spot with the beam 160 (Step S606). The end processing is processing of stopping the irradiation with the beam 160 in a case where the spot scanning irradiation method in which movement between spots is performed in a state where the beam is stopped is adopted, and is processing of proceeding to irradiation preparation for the next spot in a case where the raster scanning irradiation method in which movement between spots is performed in a state where irradiation with the beam is performed is adopted.

Then, the overall control apparatus 106 determines whether or not irradiation of the last spot with the beam 160 has ended (Step S607).

In a case where the irradiation of the last spot with the beam 160 has not ended, the overall control apparatus 106 increments n, instructs the accelerator control apparatus 107 and the irradiation control apparatus 108 to prepare irradiation of the next spot (Step S608), and returns to the processing of Step S604.

On the other hand, in a case where the irradiation of the last spot with the beam 160 has ended, the treatment on the day ends. Then, the overall control apparatus 106 determines whether or not the day is the last day. In a case where the day is not the last day, the processing of Step S601 is performed, and in a case where the day is the last day, the processing ends.

The irradiation control apparatus 108 may be directly connected to the accelerator control apparatus 107 and directly transmit various signals to the accelerator control apparatus 107.

Hereinafter, irradiation dose monitoring processing which corresponds to the processings of Steps S604 to S606 of FIG. 6, will be described in more detail.

Figure 7:
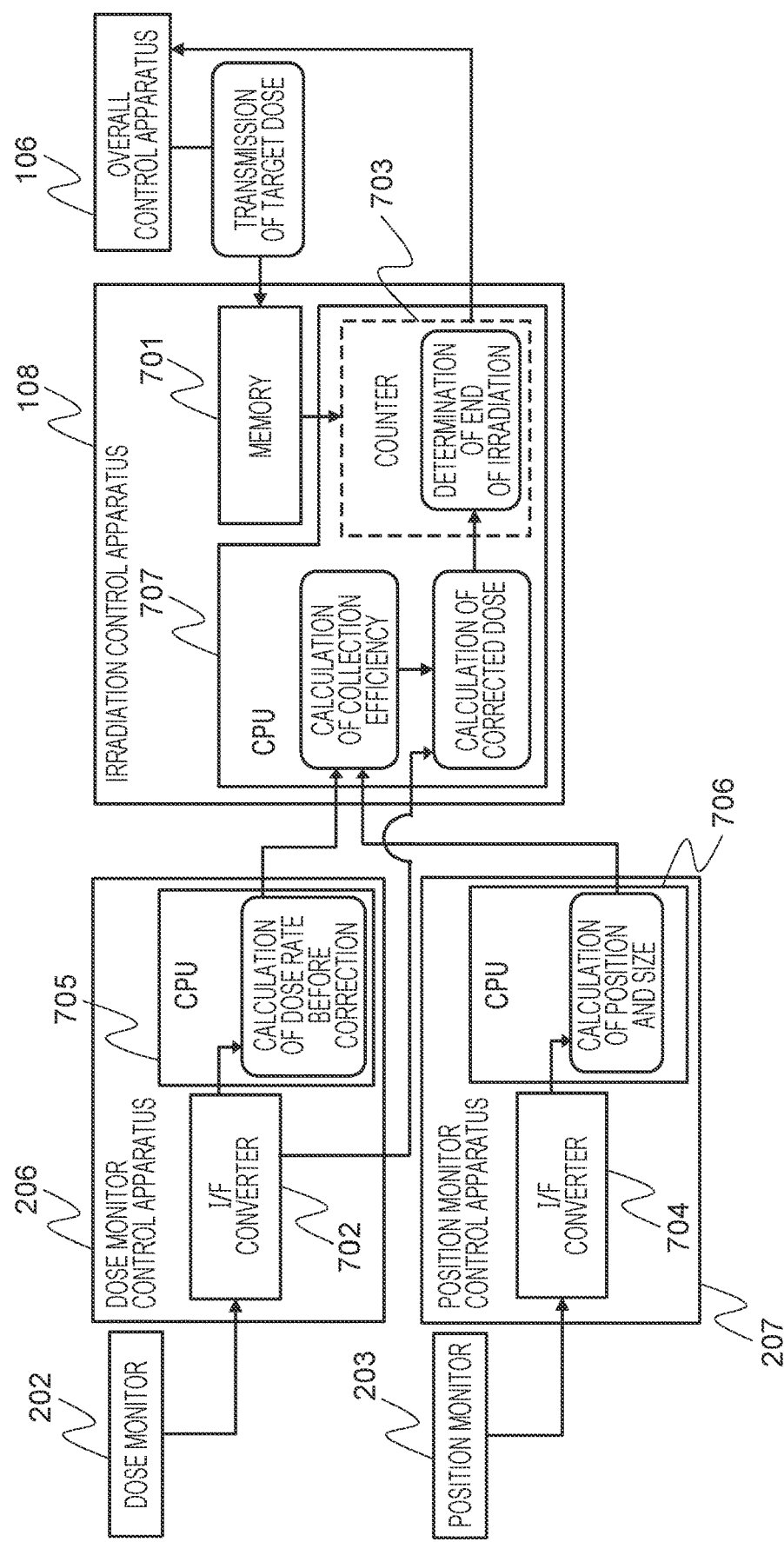
FIG. 7 is a diagram illustrating a configuration example of an irradiation control system according to the first embodiment of the present disclosure.
Figure 8:
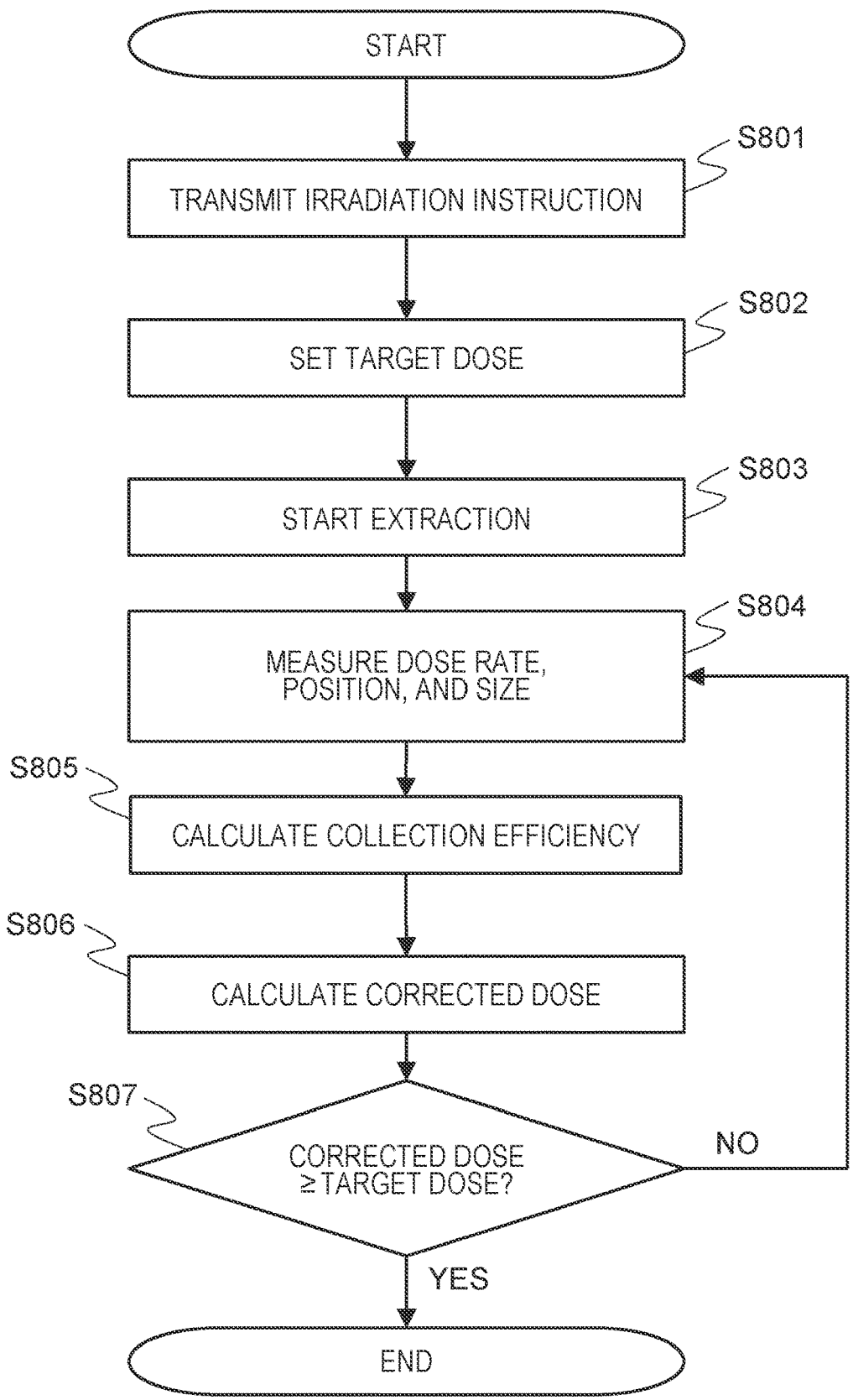
FIG. 8 is a flowchart for describing an example of monitoring processing according to the first embodiment of the present disclosure.

FIG. 7 is a diagram illustrating a configuration example of an irradiation control system including the irradiation nozzle 103 and the irradiation control apparatus 108. FIG. 8 is a flowchart for describing an example of monitoring processing performed by the irradiation control system illustrated in FIG. 7. Hereinafter, the irradiation of the n-th spot with the beam 160 will be described as an example.

As illustrated in FIG. 7, the dose monitor control apparatus 206 includes an I/F converter 702 that converts a current output from the dose monitor 202 into a pulse signal, and a CPU 705 that calculates a dose rate based on the pulse signal obtained by the conversion performed by the I/F converter 702. A pulse frequency of the pulse signal represents the dose rate. The position monitor control apparatus 207 includes an I/F converter 704 that converts a current output from the position monitor 203 into a pulse signal, and a CPU 706 that calculates the center position and the beam size of the beam 160 based on the pulse signal obtained by the conversion performed by the I/F converter 704.

The irradiation control apparatus includes a memory 701 that stores the control instruction data (the target dose for each spot) and a CPU 707. The CPU 707 includes a counter 703 that counts the number of pulses.

Once Step S604 starts, the overall control apparatus 106 first transmits an irradiation start instruction to the accelerator control apparatus 107 and the irradiation control apparatus 108 (Step S801). Once the irradiation start instruction is received, the accelerator control apparatus 107 accelerates and extracts the beam 160 according to the control instruction data stored in the memory (Step S803).

The CPU 707 of the irradiation control apparatus 108 reads the target dose corresponding to the n-th spot among the target doses stored in the memory 701 in Step S602 during a period from the reception of the irradiation start instruction to the extraction of the beam 160 by the accelerator control apparatus 107 (between Steps S801 and S803). In the present embodiment, a current output from the dose monitor 202 is converted into a pulse signal by the I/F converter 702 of the dose monitor control apparatus 206, and the number of pulses of the pulse signal represents the dose. Therefore, the CPU 707 sets the target number of pulses in the counter 703, the target number of pulses being obtained by converting the target dose into the number of pulses (Step S802).

A conversion count for converting the target dose into the target number of pulses is determined according to a characteristic of a dose measurement circuit including the dose monitor 202 and the I/F converter 702. The processing of Step S802 may be performed during a period from the end of irradiation of the previous spot ((n−1)-th spot) with the beam 160 to transmission of the irradiation start instruction for a corresponding spot.

Once the beam 160 is extracted (Step S803), the currents detected by the dose monitor 202 and the position monitor 203 during the irradiation of the target volume 151 with the beam 160 are converted into pulse signals by the I/F converters 702 and 704 in the dose monitor control apparatus 206 and the position monitor control apparatus 207, respectively. As described with reference to FIG. 3, the CPU 705 of the dose monitor control apparatus 206 calculates the dose rate of the beam 160 based on the pulse signal and transmits the dose rate to the irradiation control apparatus 108. In addition, as described with reference to FIG. 4, the CPU 706 of the position monitor control apparatus 207 calculates the center position and the beam size of the beam 160 based on a two-dimensional distribution of the pulse frequency of the pulse signal, and transmits the center position and the beam size to the irradiation control apparatus 108 (Step S804). Similarly to the conversion coefficient for the target dose, a conversion coefficient for converting a current into a pulse signal is a constant determined according to the characteristic of the dose measurement circuit.

The CPU 707 of the irradiation control apparatus 108 calculates the collection efficiency of the dose monitor 202 for the beam 160 based on the dose rate and the beam size (Step S805).

Hereinafter, a calculation method based on a theoretical formula will be described as an example of a collection efficiency calculation method.

Assuming that a spread of the beam 160 follows the Gaussian distribution, a beam current density i(r) of the beam 160 at a distance r from the center of the beam 160 is expressed by the following Formula 1 using an actual integral beam current I of the beam 160 and a beam size G. The distance r is a distance in an in-plane direction orthogonal to the traveling direction of the beam 160.

Math. 1

$$i(r) = \frac{I}{2\pi\sigma^2}\exp\left(-\frac{r^2}{2\sigma^2}\right) \quad (1)$$

Meanwhile, an integral beam current J measured by the dose monitor 202 is expressed by the following Formula 2 using the beam current density i(r) and local collection efficiency f(r) in a minute region in the dose monitor 202.

Math. 2

$$J=\int_0^\infty f(r)i(r)2\pi r\,dr \quad (2)$$

According to Boag's theory, the local collection efficiency f(r) and the beam current density i(r) have a relationship represented by Formula 3.

Math. 3

$$f(r) = \frac{1}{1+\frac{\xi^{\sim}(r)^2}{6}}, \xi(r) = k\frac{d^2\sqrt{i(r)}}{V} \equiv \sqrt{6Ki(r)} \quad (3)$$

Here, k is $2.01\times10^7$ [v/(m$^{0.5}$A$^{0.5}$)], V is a fed voltage to be fed to the dose monitor 202, and d is a constant determined according to the structure of the dose monitor 202. For example, in a case where the dose monitor 202 includes one high-voltage electrode 303 and one collector electrode 304, d is an interval between the high-voltage electrode 303 and the collector electrode 304. By substituting Formulae 1 and 3 into Formula 2 and integrating Formula 2, collection efficiency F of the entire dose monitor 202 is expressed by Formula 4 as a function of the integral beam current J.

Math. 4

$$F \equiv \frac{J}{I} = \frac{K}{2\pi\sigma^2}\frac{J}{\exp\left(\frac{K}{2\pi\sigma^2}J\right)-1} \quad (4)$$

The integral beam current J is obtained by integrating a constant coefficient with the dose rate calculated by the dose monitor control apparatus 206, and the beam size σ is calculated by the position monitor control apparatus 207. Therefore, the CPU 707 of the irradiation control apparatus 108 can calculate the collection efficiency F by substituting these values into Formula 4.

The collection efficiency calculation method described above is merely an example, and is not limited to this method. For example, although it has been assumed above that the spread of the beam 160 follows the Gaussian distribution, in a case where the spread of the beam 160 is a distribution defined according to the integral beam current and the beam size, it may be assumed that the spread of the beam 160 follows the Lorentz distribution or the like.

In addition, for example, a method using a collection efficiency table indicating a relationship between the dose rate, the beam size σ, and the collection efficiency may be used instead of the method of calculating the collection efficiency by using Formula (4) that is a theoretical formula. In this method, the CPU 707 of the irradiation control apparatus 108 calculates the collection efficiency by referring to the collection efficiency table created in advance.

Figure 9:
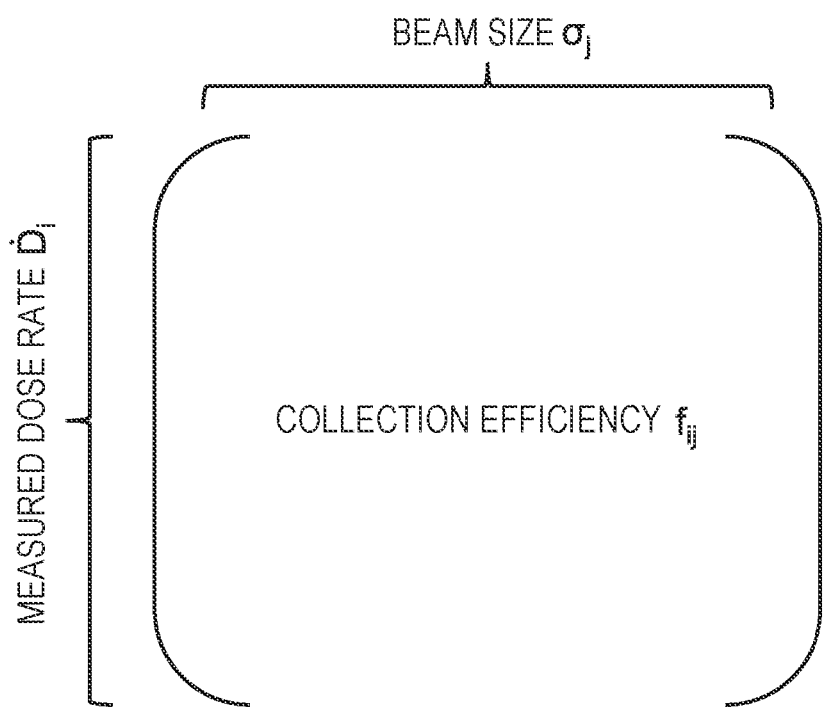
FIG. 9 is a conceptual diagram of a collection efficiency table according to the first embodiment of the present disclosure.

FIG. 9 is a diagram illustrating an example of the collection efficiency table. A collection efficiency table 900 illustrated in FIG. 9 is a matrix table in which the row corresponds to the dose rate and the column corresponds to the beam size, and each element represents the collection efficiency for the dose rate and the beam size corresponding to its row and column.

Examples of a method of creating the collection efficiency table include a method in which measurement is performed by the dose monitor 202 on a beam whose dose rate and beam size are known, and processing of calculating the collection efficiency by comparing an ideal dose rate with the measured dose rate is repeatedly performed while changing the dose rate and the beam size.

The description returns to the operation in FIGS. 7 and 8. Once the processing of Step S805 ends, the CPU 707 of the irradiation control apparatus 108 multiplies the pulse frequency of the pulse signal from the dose monitor control apparatus 206 by a reciprocal of the collection efficiency to acquire a corrected pulse frequency corresponding to a corrected dose rate that is a dose rate that takes into consideration a variation in collection efficiency. The CPU 707 counts the corrected number of pulses corresponding to the corrected dose obtained by correcting the measured dose obtained by measuring the dose applied to the n-th spot with the collection efficiency, by integrating the corrected pulse frequency using the counter 703 (Step S806).

The CPU 707 of the irradiation control apparatus 108 determines whether or not the corrected dose has reached the target dose by determining whether or not the corrected number of pulses has reached the target number of pulses read from the memory 701 (Step S807). In a case where the corrected dose has not reached the target dose, the processing of Step S804 is performed again, and in a case where the corrected dose has reached the target dose, the irradiation dose monitoring processing ends, and the processing of Step S606 in FIG. 6 is performed.

Next, effects of the present embodiment will be described.

According to the present embodiment, the dose monitor 202 measures the dose of the beam 160. The position monitor 203 measures the beam size of the beam 160. The irradiation control apparatus 108 calculates the measurement characteristic of the dose monitor 202 based on the dose and the beam size of the beam 160, and controls the irradiation of the patient 150 with the beam 160 based on the measurement characteristic and the dose. Accordingly, since the irradiation of the patient 150 with the beam 160 is controlled based on the measurement characteristic of the dose monitor 202 calculated based on the actually measured dose and beam size of the beam 160, it is possible to control the dose of the beam 160 more accurately with which the patient 150 is irradiated.

Furthermore, in the present embodiment, the irradiation control apparatus 108 calculates a corrected dose obtained by correcting the dose based on the measurement characteristic, and performs processing of ending the irradiation with the beam 160 in a case where an integral value of the corrected dose has reached the target dose. It is sufficient if the setting of the target dose and the like is performed in the same manner as in the related art except for correcting the dose. Therefore, it is not necessary to change a processing system, that is, it is not necessary to add and change an existing hardware apparatus, and it is possible to prevent an additional cost from being incurred.

In the present embodiment, the collection efficiency of the ionization chamber is used as the measurement characteristic of the dose monitor 202. Therefore, the general dose monitor 202 can be used, and it is thus possible to prevent an additional cost from being incurred.

Second Embodiment

Next, a particle therapy system and an irradiation control apparatus according to a second embodiment of the present disclosure will be described with reference to FIGS. 10 to 12. Hereinafter, differences from the first embodiment will be mainly described. The same components as those in the first embodiment are denoted by the same reference signs.

An overall configuration of a particle therapy system 100 according to the second embodiment is similar to the overall configuration of the particle therapy system 100 according to the first embodiment illustrated in FIG. 1. However, in the present embodiment, an irradiation control apparatus 108 calculates a corrected target dose obtained by correcting a target dose instead of correcting a dose based on collection efficiency of a dose monitor 202. In a case where an integral value of the dose measured by the dose monitor 202 has reached the corrected target dose, the irradiation control apparatus 108 performs end processing of ending irradiation with a beam 160. The corrected target dose is calculated for each spot, and the collection efficiency used to calculate the corrected target dose for each spot is calculated based on the dose and a beam size of the beam 160 with which a reference spot, which is a previous irradiated spot, has been irradiated. In the present embodiment, the collection efficiency for each spot is calculated based on the dose and the beam size of the beam 160 with which a previous irradiated spot has been irradiated.

In a case where a difference in characteristic of the beam 160 with respect to each of the reference spot and the irradiation spot is sufficiently small, the collection efficiency is calculated with high accuracy also in the present embodiment, and highly accurate irradiation control can be performed. For example, in a case where a periodic variation scale of a beam parameter is longer than an irradiation time for one spot and a difference in beam parameter between adjacent spots is smaller than a difference between an irradiation instruction and actual irradiation, it is possible to calculate the collection efficiency with higher accuracy than that in a case of calculating the collection efficiency based on a prescription, by referring to an average value of the beam parameters for the immediately previous spot.

The overall flow of treatment processing of treating a patient 150 in the present embodiment is similar to the overall flow of the treatment processing described with reference to FIG. 6. However, since the dose and the beam size of the beam 160 for calculating the corrected target dose cannot be obtained for the first spot irradiated with the beam 160 first, the irradiation control apparatus 108 performs additional processing for reducing an influence of an error of the dose applied to the first spot on treatment quality at the time of creating a prescription in Step S602.

The additional processing is processing of determining, as the first spot, a spot satisfying a predetermined condition among a plurality of spots obtained by dividing a target volume 151. For example, in the additional processing, the first spot is determined based on the target volume 151.

Figure 10:
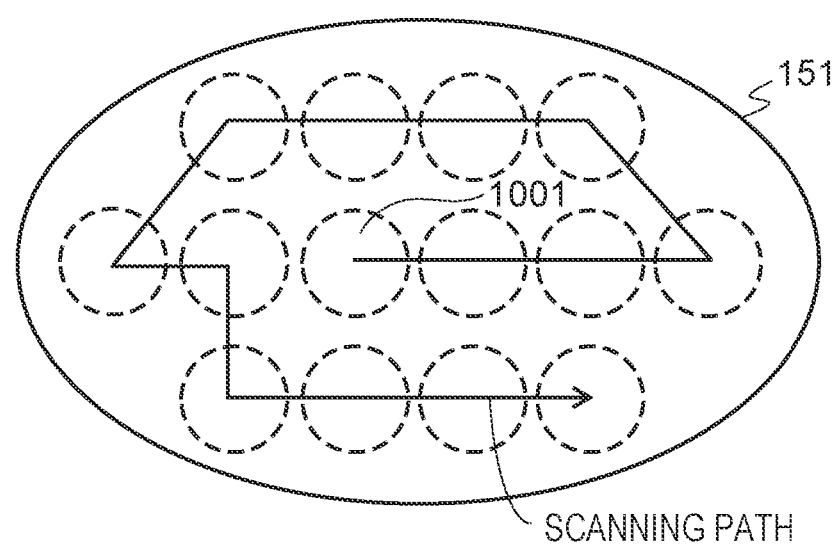
FIG. 10 is a diagram illustrating an example of a method of determining the first spot according to a second embodiment of the present disclosure.

FIG. 10 is a diagram illustrating an example of the first spot. The example in FIG. 10 is an example in which the first spot is set to a spot 1001 closest to the center of the target volume 151. In this case, since it is considered that there is no or few normal tissues in the vicinity of the spot 1001, the influence of the error of the dose on the treatment quality can be reduced.

The first spot illustrated in FIG. 10 is merely an example, and the first spot is not limited thereto. For example, the first spot may be a spot whose distance from a predetermined organ is a certain value or more. In addition, the first spot set by an arbitrary method may be divided into a plurality of subdivided spots, and any of the subdivided spots may be reset as the first spot. In this case, the target dose for the subdivided spot can be reduced, and thus, the dose applied to the subdivided spot can be reduced. As a result, the influence of the error of the dose on the treatment quality can be reduced.

The additional processing may be automated by a program of the irradiation control apparatus 108, or may be processing of displaying the target volume 151 and each spot to make an operator perform selection.

Hereinafter, irradiation dose monitoring processing according to the second embodiment (processings of Steps S604 to S606 of FIG. 6) will be described in more detail.

Figure 11:
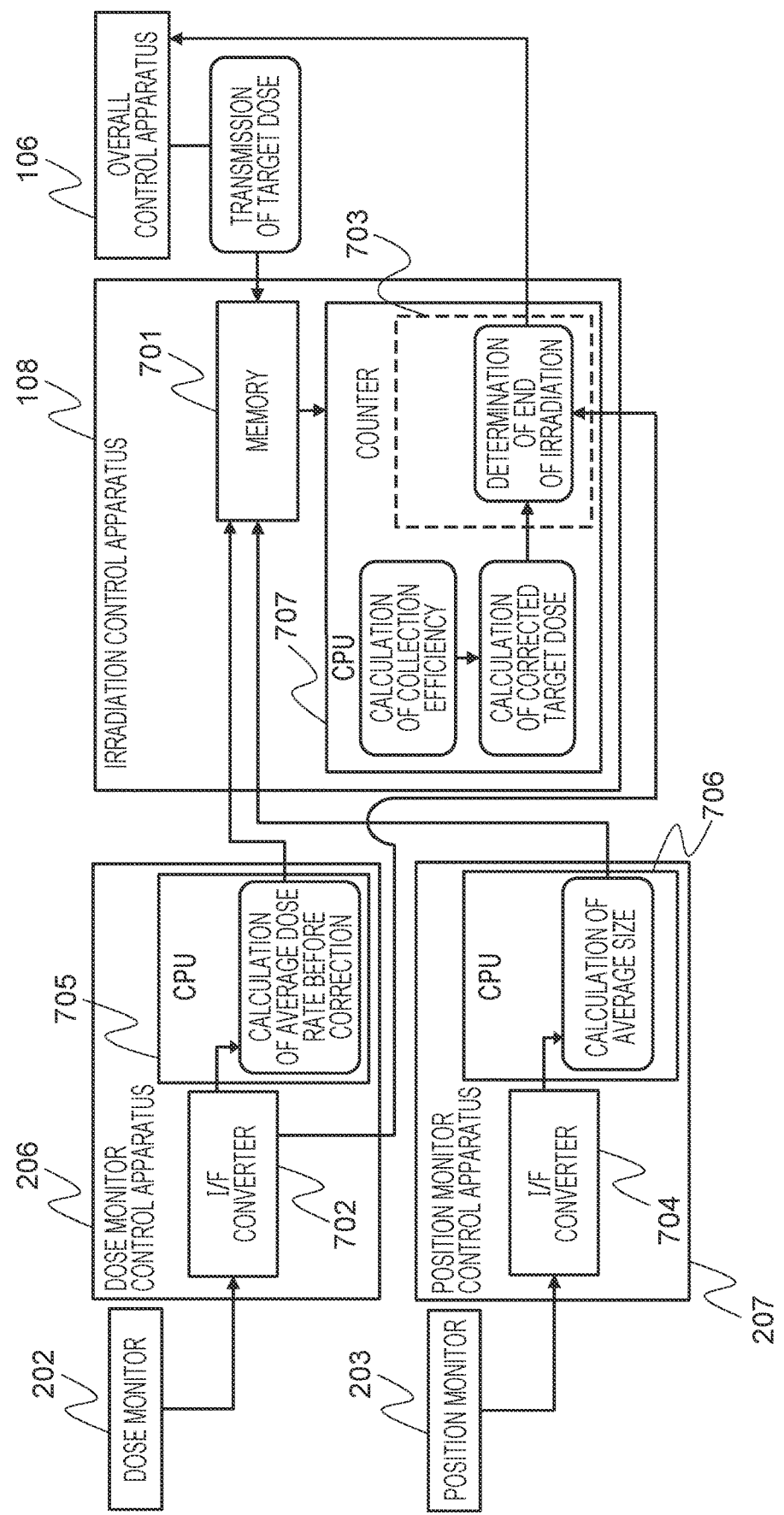
FIG. 11 is a diagram illustrating a configuration of an irradiation control system according to the second embodiment of the present disclosure.
Figure 12:
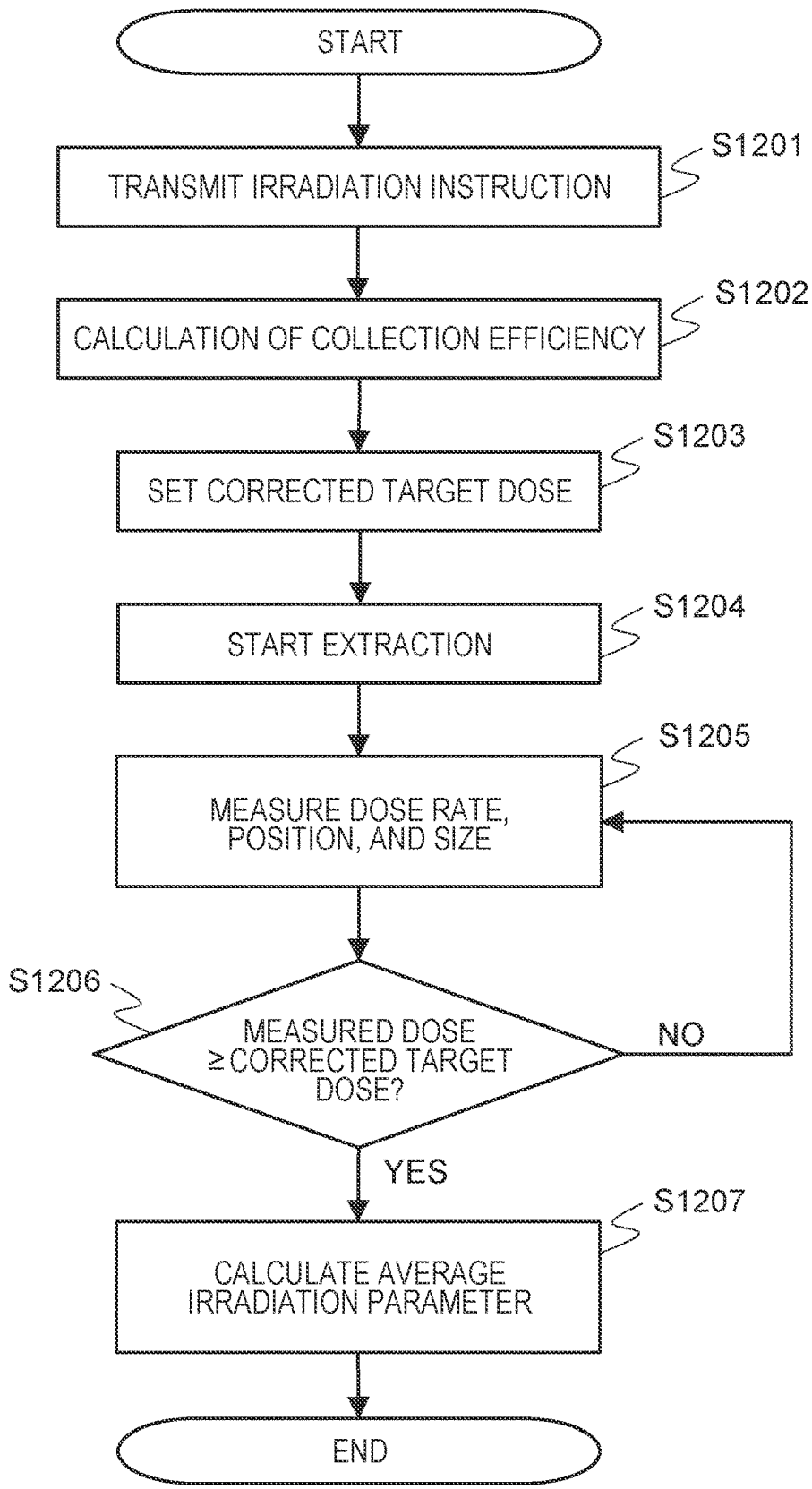
FIG. 12 is a flowchart for describing an example of monitoring processing according to the second embodiment of the present disclosure.

FIG. 11 is a diagram illustrating a configuration example of an irradiation control system including an irradiation nozzle 103 and the irradiation control apparatus 108. FIG. 12 is a flowchart for describing an example of monitoring processing performed by the irradiation control system illustrated in FIG. 11. Hereinafter, irradiation of the n-th spot with the beam 160 will be described as an example.

After starting the irradiation of the n-th spot, an overall control apparatus 106 transmits an irradiation start instruction to an accelerator control apparatus 107 and the irradiation control apparatus 108 (Step S1201). Once the irradiation start instruction is received, the accelerator control apparatus 107 accelerates and extracts the beam 160 according to control instruction data stored in a memory (Step S1204).

A CPU 707 of the irradiation control apparatus 108 performs the following Steps S1202 and S1203 during a period from the reception of the irradiation start instruction to the extraction of the beam 160 by the accelerator control apparatus 107.

First, the CPU 707 calculates the collection efficiency of the dose monitor 202 based on an average dose rate and an average size of the beam 160 with which the immediately previous spot ((n−1)-th spot) stored in a memory 701 is irradiated (Step S1202). The average dose rate is an average value of the dose rates of the beam 160 with which the immediately previous spot is irradiated, and the average size is an average value of the beam sizes of the beam 160 with which the immediately previous spot is irradiated. The average dose rate is an average value of dose rates that have not been corrected based on the collection efficiency. Similarly to the first embodiment, the collection efficiency may be calculated by a method using Theoretical Formula (4) or a method using the table as illustrated in FIG. 9.

In a case where n=1, that is, in a case where the first spot is irradiated with the beam 160, there is no average dose rate and average size corresponding to the immediately previous spot. Therefore, the CPU 707 may set a fixed value (for example, 1) as the collection efficiency, or may approximate the collection efficiency based on the average dose rate and the average size estimated based on a prescription.

Next, the CPU 707 reads the target dose for the n-th spot from the memory 701, and calculates a corrected target dose obtained by correcting the target dose based on the collection efficiency. The CPU 707 sets the target number of pulses in a counter 703, the target number of pulses being obtained by converting the corrected target dose into the number of pulses (Step S1203).

Once the beam 160 is extracted (Step S1204), currents detected by the dose monitor 202 and a position monitor 203 during the irradiation of the target volume 151 with the beam 160 are converted into pulse signals by I/F converters 702 and 704 in a dose monitor control apparatus 206 and a position monitor control apparatus 207, respectively, and the pulse signals are output. The CPU 707 of the irradiation control apparatus 108 transmits the pulse signal output from the I/F converter 702 to the counter 703 to integrate the number of pulses. That is, in the present embodiment, unlike the first embodiment, the dose rate is not corrected based on the collection efficiency. In addition, a CPU 706 of the position monitor control apparatus 207 calculates a center position and the beam size of the beam 160 based on the pulse signal output from the I/F converter 702 (Step S1205).

The CPU 707 of the irradiation control apparatus 108 determines whether or not the dose applied to the n-th spot has reached the corrected target dose by determining whether or not the integrated number of pulses has reached the corrected target number of pulses for the n-th spot read from the memory 701 (Step S1206).

In a case where the dose has not reached the corrected target dose, the processing returns to Step S1205. On the other hand, in a case where the dose has reached the corrected target dose, a CPU 705 of the dose monitor control apparatus 206 calculates, as an average dose rate before correction, an average value of the dose rates of the beam 160 with which the first spot is irradiated, and records the average value in the memory 701 of the irradiation control apparatus 108. In addition, the CPU 706 of the position monitor control apparatus 207 calculates, as an average size, an average value of the beam sizes of the beam 160 with which the first spot is irradiated, records the average value in the memory 701 of the irradiation control apparatus 108 (Step S1207), and ends the processing. The average dose rate before correction and the average size may be collectively referred to as an average irradiation parameter. In addition, the average dose rate before correction is a name for convenience, and in the present embodiment, the dose rate is not corrected.

In the above operation, a timing for calculating the average irradiation parameter and the collection efficiency is not limited to the timing described with reference to FIG. 12. For example, the average irradiation parameter may be calculated based on the number of pulses integrated up to a predetermined time point before the irradiation with the beam 160 ends, or the collection efficiency may be calculated during a period from a timing at which the irradiation with the beam 160 ends to a timing at which irradiation of the next spot starts.

In the above example, the reference spot refers to the immediately previous spot of a target spot, but the reference spot is not limited to this example. For example, the irradiation control apparatus 108 may select, as the reference spot, a spot at which the beam parameter is closest to the beam 160 with which the target spot is irradiated based on a variation trend of the beam parameter of the beam 160.

Next, effects of the present embodiment will be described.

As described above, according to the present embodiment, the irradiation control apparatus 108 calculates a corrected target dose obtained by correcting a predetermined target dose based on a measurement characteristic, and performs processing of ending irradiation with the beam 160 in a case where an integral value of the dose has reached the corrected target dose. Therefore, similarly to the first embodiment, it is possible to set the target dose in the same manner as in the related art, and thus, it is not necessary to change the processing system. Therefore, it is not necessary to add or change an existing hardware apparatus, and it is possible to prevent an additional cost from being incurred.

In addition, in the present embodiment, the irradiation control apparatus 108 calculates the corrected target dose for each spot based on the dose and the beam size of the beam 160 with which a previous irradiated spot has been irradiated. Accordingly, since it is not necessary to correct the dose of the beam 160 in real time, it is possible to suppress occurrence of a delay in determination to end the irradiation with the beam 160 due to a processing time for the correction, and it is possible to suppress excessive irradiation.

In addition, in the present embodiment, the irradiation control apparatus 108 calculates the corrected target dose for each spot based on the dose and the beam size of the beam 160 with which the immediately previous spot of the corresponding spot is irradiated. Therefore, it is possible to calculate the corrected target dose based on the dose and the beam size of the beam 160 considered to be closest to the characteristics of the beam 160, and thus, it is possible to control the dose of the beam 160 more accurately with which the patient 150 is irradiated.

Furthermore, in the present embodiment, a spot satisfying a predetermined condition is set as the first spot to be irradiated with the beam 160 first. Therefore, it is possible to reduce the influence of the error of an irradiation dose for the first spot on the treatment quality.

Note that the present disclosure is not limited to the above-described embodiments and includes various modifications. The above-described embodiments have been described in detail in order to explain the present invention in an easy-to-understand manner, and the present invention is not necessarily limited to those having all the configurations described. Further, a part of a configuration of an embodiment can also be replaced with a configuration of another embodiment, and a configuration of an embodiment can be added to a configuration of another embodiment. In addition, a part of a configuration of each embodiment can be added with another configuration, can be deleted, and can be replaced with another configuration.

What is claimed is:

1. A particle therapy system that irradiates a subject with a particle beam, the particle therapy system comprising:
   a dose monitor that measures a dose of the particle beam;
   a position monitor that measures a beam size of the particle beam; and
   an irradiation control apparatus that calculates a measurement characteristic of the dose monitor based on the dose and the beam size, and controls irradiation of the subject with the particle beam based on the measurement characteristic and the dose, wherein
   the irradiation control apparatus calculates a corrected dose obtained by correcting the dose based on the measurement characteristic, and performs processing of ending the irradiation with the particle beam in a case where an integral value of the corrected dose has reached the target dose, or
   the irradiation control apparatus calculates a corrected target dose obtained by correcting a predetermined target dose based on the measurement characteristic, and performs processing of ending the irradiation with the particle beam in a case where an integral value of the dose has reached the corrected target dose.

2. The particle therapy system according to claim 1, wherein
   the irradiation control apparatus calculates the corrected dose obtained by correcting the dose based on the measurement characteristic, and performs the processing of ending the irradiation with the particle beam in the case where the integral value of the corrected dose has reached the target dose.

3. The particle therapy system according to claim 2, wherein
   the target dose is set in advance for each of a plurality of spots in the subject to be irradiated with the particle beam, and
   the irradiation control apparatus sequentially irradiates each of the plurality of spots with the particle beam, and in a case where the corrected dose of the particle beam with which any one of the spots is irradiated has reached the target dose of the spot, the irradiation control apparatus performs processing of ending the irradiation of the spot with the particle beam.

4. The particle therapy system according to claim 1, wherein
   the irradiation control apparatus calculates the corrected target dose obtained by correcting the predetermined target dose based on the measurement characteristic, and performs the processing of ending the irradiation with the particle beam in the case where the integral value of the dose has reached the corrected target dose.

5. The particle therapy system according to claim 4, wherein
   the target dose is set in advance for each of a plurality of spots in the subject to be irradiated with the particle beam, and
   the irradiation control apparatus sequentially irradiates each of the plurality of spots with the particle beam, and in a case where the dose of the particle beam with which any one of the spots is irradiated has reached the corrected target dose for the spot, the irradiation control apparatus performs processing of ending the irradiation of the spot with the particle beam.

6. The particle therapy system according to claim 5, wherein
   the irradiation control apparatus calculates the corrected target dose for each spot based on the dose and the beam size of the particle beam with which a previous irradiated minute region has been irradiated.

7. The particle therapy system according to claim 6, wherein
   the irradiation control apparatus calculates the corrected target dose for each spot based on the dose and the beam size of the particle beam with which an immediately previous irradiated minute region has been irradiated.

8. The particle therapy system according to claim 5, wherein
   the irradiation control apparatus determines a spot to be irradiated with the particle beam first based on a target volume which is an irradiation region to be irradiated with the particle beam.

9. The particle therapy system according to claim 1, wherein
   the dose monitor is an ionization chamber, and
   the measurement characteristic is collection efficiency of the ionization chamber.

10. An irradiation control apparatus connected to a dose monitor that measures a dose of a particle beam with which a subject is irradiated, and to a position monitor that measures a beam size of the particle beam, wherein
    the irradiation control apparatus calculates a measurement characteristic of the dose monitor based on the dose and the beam size, and controls irradiation of the subject with the particle beam based on the measurement characteristic and the dose, wherein
    the irradiation control apparatus calculates a corrected dose obtained by correcting the dose based on the measurement characteristic, and performs processing of ending the irradiation with the particle beam in a case where an integral value of the corrected dose has reached the target dose, or
    the irradiation control apparatus calculates a corrected target dose obtained by correcting a predetermined target dose based on the measurement characteristic, and performs processing of ending the irradiation with the particle beam in a case where an integral value of the dose has reached the corrected target dose.

11. An irradiation control method performed by a particle therapy system that irradiates a subject with a particle beam, the irradiation control method comprising:
    measuring a dose of the particle beam;
    measuring a beam size of the particle beam;
    calculating a measurement characteristic for measuring the dose based on the dose and the beam size;
    controlling irradiation of the subject with the particle beam based on the measurement characteristic and the dose; and
    calculating a corrected dose obtained by correcting the dose based on the measurement characteristic, and performing processing of ending the irradiation with the particle beam in a case where an integral value of the corrected dose has reached the target dose, or calculating a corrected target dose obtained by correcting a predetermined target dose based on the measurement characteristic, and performing processing of ending the irradiation with the particle beam in a case where an integral value of the dose has reached the corrected target dose.

* * * * *